Figure 1:
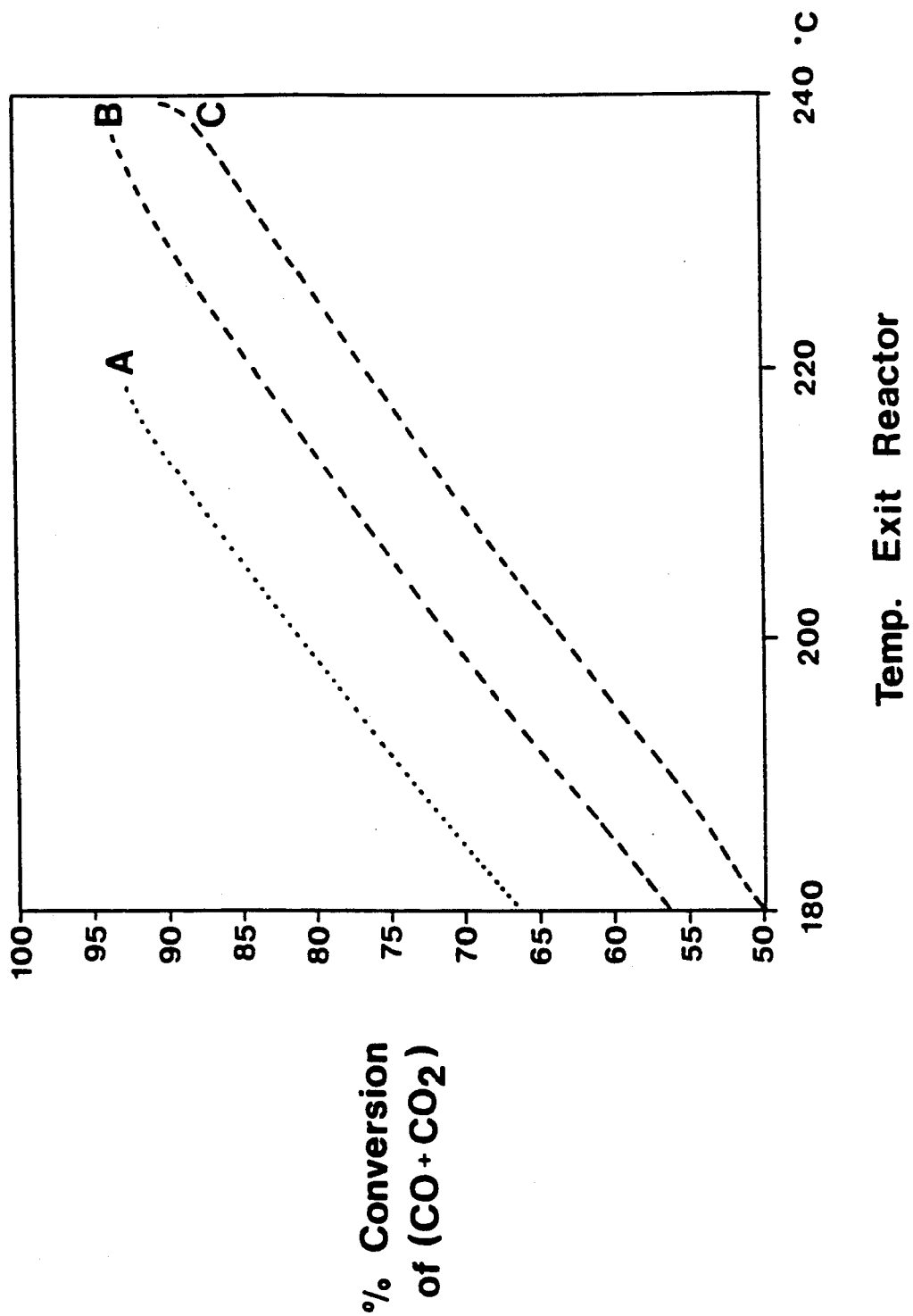

United States Patent [19]

Topsoe et al.

[11] Patent Number: 5,262,443
[45] Date of Patent: Nov. 16, 1993

[54] METHOD OF PREPARING METHANOL

[75] Inventors: Haldor F. A. Topsoe, Vedbaek; John B. Hansen, Helsinger, both of Denmark

[73] Assignee: Haldor Topsoe A/S, Denmark

[21] Appl. No.: 942,110

[22] Filed: Sep. 8, 1992

Related U.S. Application Data

[63] Continuation of Ser. No. 671,218, Mar. 18, 1991, abandoned.

[30] Foreign Application Priority Data

Mar. 19, 1990 [DK] Denmark .................. 07010/90

[51] Int. Cl.$^5$ .................................. C07C 27/06
[52] U.S. Cl. ........................... 518/728; 518/713
[58] Field of Search ...................... 518/713, 728

[56] References Cited

U.S. PATENT DOCUMENTS

| | | | |
|---|---|---|---|
| 4,436,833 | 3/1984 | Broecker et al. | 518/713 |
| 4,670,473 | 6/1987 | Walker et al. | 518/712 |
| 4,731,387 | 3/1988 | Westerterp | 518/713 |
| 4,843,101 | 6/1989 | Klier et al. | 518/713 |

FOREIGN PATENT DOCUMENTS 2025418  1/1980  United Kingdom .............. 518/713

OTHER PUBLICATIONS

Kuczynski et al., Chemical Engineering Science 42 No. 8 pp. 1887-1898, 1987.

*Primary Examiner*—Howard T. Mars
*Attorney, Agent, or Firm*—Ostrolenk, Faber, Gerb & Soffen

[57] ABSTRACT

A method of preparing methanol by reacting synthesis gas comprising hydrogen and carbon oxides in a fixed bed of methanol synthesis catalyst. The reaction of the synthesis gas is conducted under conditions where condensation of methanol occurs on the catalyst. Pressure, temperature and/or space velocity of the gas at the exit of the catalyst bed are adjusted to where conversion levels of the gas leads to formation of liquid methanol in the catalyst bed by exceeding the dew point of the reaction mixture.

12 Claims, 5 Drawing Sheets

METHOD OF PREPARING METHANOL

This is a continuation of application Ser. No. 07/671,218 filed on Mar. 18, 1991.

The present invention relates to a method of preparing methanol by reacting synthesis gas of hydrogen and carbon oxides (CO, $CO_2$) in the presence of a methanol synthesis catalyst.

Industrial preparation of methanol is based on the strongly exothermic equilibrium reaction:

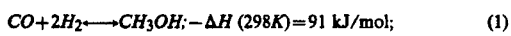

$$CO + 2H_2 \rightleftharpoons CH_3OH; -\Delta H (298K) = 91 \text{ kJ/mol}; \quad (1)$$

which thermodynamically is less favourable to methanol and for reasonable reaction yields only possible by use of a selective catalyst that promotes the desired reaction and inhibits side reactions. At present only catalysts based on $CuO/ZnO/Al_2O_3$ are used in the industrial preparation of methanol.

In conventional methanol synthesis processes hydrogen and carbon oxides containing synthesis gas is usually obtained by steam reforming or autothermal reforming of hydrocarbon feedstock in the front end of a methanol plant. The reformed gases are cooled and adjusted to methanol synthesis gas with a ratio of $H_2$:CO of usually about 2.25:1. The synthesis gas thereby obtained is preheated and compressed to a pressure and temperature, at which the gas reacts in a subsequent methanol converter. Conventional methanol converters consist of a pressure vessel provided with a methanol synthesis catalyst bed, quench gas units and/or heat exchangers to preheat the synthesis gas and to control the heat of reaction. The gas is introduced into the catalyst bed typically at about 200°–300° C. at a standard space velocity of about 8000 $Nm^3/h$. Crude methanol is condensed from the effluent converter gas and unreacted gas recycled to the inlet of the reactor.

There have been a number of alternative processes suggested in the art for converting methanol synthesis gas to improve the reaction conditions, including different catalyst compositions and inert diluents for immersing or cooling the catalyst (see e.g. U.S. Pat. No. 4,529,738; DEOffenlegungsschrift No. 3,522,302 and patent application No. 84.4675).

Major improvements to methanol synthesis efficiencies, however, result from overcoming equilibrium limitations by separating reactants and produced methanol as it forms in the catalyst bed.

In situ separation of reactants and methanol is disclosed in U.S. Pat. No. 4,731,387. In a gas solid trickle flow reactor produced methanol is removed in the catalyst bed by adsorption on amorphous low-alumina cracking catalyst, which is introduced into the reactor from a top storage vessel to be operated batch-wise. The adsorbent flows over a fixed bed of conventional Cu—ZnO—$Al_2O_3$ methanol synthesis catalyst and removes the methanol formed on the catalyst from unreacted synthesis gas. After having passed the reactor and a cooler the adsorbent is received in a bottom vessel and methanol is recovered from the adsorbent. According to the patent specification of U.S. Pat. No. 4,731,387, substantially all of the methanol produced in the catalyst bed is adsorbed and methanol yields of nearly 100% are achieved.

Drawbacks of the trickle flow reactor are operational difficulties in solids circulation systems resulting in the need of large storage vessels for the adsorbent to be operated batch-wise, and energy consuming recovery of adsorbed methanol from the adsorbent.

It has now surprisingly been found that the above drawbacks can be avoided when operating under reaction conditions, where liquid methanol is formed in situ on the methanol synthesis catalyst during the synthesis.

Accordingly, it is an object of the present invention to provide a method of preparing methanol by reacting synthesis gas comprising hydrogen and carbon oxides in a fixed bed of methanol synthesis catalyst, the improvement of which comprises reacting the synthesis gas under conditions where condensation of methanol occurs on the catalyst.

At condensing conditions the thermodynamic gas phase equilibrium boundary for methanol formation has been overcome and methanol yields approaching 100% in the catalyst bed effluent can be reached by once-through operation.

Suitable catalysts for the inventive method are any of the known methanol synthesis catalysts, which are applicable in fixed bed manner. Preferred catalysts are those based on the oxides of Zn and Cu, such as the commercial methanol catalyst sold by Haldor Topsoe A/S, Denmark, under the trade-name "MK-101". The catalyst may be in any form, such as particles, pellets or tablets, which usually are employed in conventional fixed bed methanol converters.

Cooling of the catalyst bed may be provided by external cooling of the converter resulting in substantially isothermal operation, or intermediate cooling between subsequent adiabatic catalyst beds in one or more methanol converters.

Under certain reaction conditions the temperature in the catalyst bed may exceed acceptable levels. For instance, by operating in once-through mode with CO-rich synthesis gas high temperatures at the inlet of the catalyst bed due to high reaction rates may cause damage of the catalyst or lead to unacceptable high levels of by-product formation. In order to reduce the rate of reaction and thereby detrimental temperature increases, it may be necessary at certain conditions to introduce methanol along with synthesis gas.

Thus in one embodiment of the invention a part of the condensed methanol as prepared in the catalyst bed is recycled from the catalyst bed effluent to the inlet of the catalyst bed. The amount of recycled liquid methanol depends on the temperature in the catalyst bed.

Thereby, the recycle stream of liquid methanol has not to be cooled and reheated, only re-evaporated before the stream is introduced into the methanol reactor. Recycling of liquid methanol only incurs small operating costs for recompression as methanol is pumped in the liquid state.

The liquid methanol product is recovered from the catalyst bed effluent by cooling and phase separation from unconverted synthesis gas.

Reaction conditions at which methanol condenses in the catalyst bed depend on the actual composition of the synthesis gas introduced into the bed. Thus, the pressure, temperature and/or space velocity of the gas at the exit of the catalyst bed have to be adjusted to critical values, where conversion levels of the gas lead to formation of liquid methanol, when maintaining the temperature of the catalyst bed below the dew point temperature of the methanol and, thereby, exceeding the dew point in the reaction gas. Space velocities of 1,071 $h^{-1}$ and 1,166 $h^{-1}$ are preferred.

From Tables 1-3 and the accompanying drawings it will be apparent at which pressure and exit temperature condensation of methanol in the catalyst bed occurs for three different synthesis gas compositions.

TABLE 1

Synthesis gas composition:
CO 29.2 vol. %
CO2 3.0 vol. %
CH4 0.3 vol. %
H2 67.5 vol. %
Volume ratio: CO:CO2:H2 1:0.1:2.3

| Pressure MPa | Temp. °C. at reactor exit | Dew Point °C. | Conversion of CO + CO2 to methanol at gas phase equilibrium, % |
|---|---|---|---|
| 12.5 | 170 | 238.8 | 90.96 |
| 12.5 | 180 | 239.1 | 90.37 |
| 12.5 | 190 | 239.3 | 89.60 |
| 12.5 | 200 | 238.4 | 88.57 |
| 12.5 | 210 | 236.5 | 87.23 |
| 12.5 | 220 | 233.8 | 85.51 |
| 12.5 | 230 | 230.6 | 83.47 |
| 12.5 | 240 | 226.5 | 80.90 |
| 10.0 | 170 | 229.9 | 90.22 |
| 10.0 | 180 | 228.5 | 89.44 |
| 10.0 | 190 | 226.7 | 88.38 |
| 10.0 | 200 | 224.3 | 86.97 |
| 10.0 | 210 | 221.4 | 85.15 |
| 10.0 | 220 | 217.8 | 82.87 |
| 10.0 | 230 | 213.7 | 80.21 |
| 10.0 | 240 | 208.7 | 76.92 |
| 7.5 | 170 | 212.1 | 89.11 |
| 7.5 | 180 | 210.2 | 87.93 |
| 7.5 | 190 | 207.7 | 86.34 |
| 7.5 | 200 | 204.7 | 84.29 |
| 7.5 | 210 | 200.9 | 81.71 |
| 7.5 | 220 | 196.5 | 78.57 |
| 7.5 | 230 | 191.5 | 74.95 |
| 7.5 | 240 | 185.6 | 70.60 |

TABLE 2

Feed gas composition:
CO 0 vol. %
CO2 25 vol. %
CH4 0 vol. %
H2 75 vol. %
Volume ratio: CO2:H2 1:3

| Pressure MPa at reactor exit | Temp. °C. at reactor exit | Dew Point °C. | Conversion of CO + CO2 to methanol at gas phase equilibrium, % |
|---|---|---|---|
| 10.0 | 170 | 225.8 | 60.48 |
| 10.0 | 180 | 221.8 | 57.42 |
| 10.0 | 190 | 217.8 | 54.32 |
| 10.0 | 200 | 213.7 | 51.18 |
| 10.0 | 210 | 209.6 | 48.03 |
| 10.0 | 220 | 205.8 | 44.86 |
| 10.0 | 230 | 201.8 | 41.94 |
| 10.0 | 240 | 197.8 | 38.73 |
| 10.0 | 250 | 191.0 | 35.50 |
| 10.0 | 260 | 109.3 | 32.74 |
| 10.0 | 270 | 186.8 | 28.94 |
| 10.0 | 280 | 183.6 | 25.63 |
| 10.0 | 290 | 180.8 | 22.35 |
| 10.0 | 300 | 178.4 | 19.17 |

TABLE 3

Feed gas composition:
CO 49 vol. %
CO2 2 vol. %
CH4 0 vol. %
H2 49 vol. %
Volume ratio: CO:CO2:H2 1:0.04:1

| Pressure MPa at reactor exit | Temp. °C. at reactor exit | Dew Point °C. | Conversion of CO + CO2 to methanol at gas phase equilibrium, % |
|---|---|---|---|
| 10.0 | 170 | 204.3 | 46.87 |

TABLE 3-continued

Feed gas composition:
CO 49 vol. %
CO2 2 vol. %
CH4 0 vol. %
H2 49 vol. %
Volume ratio: CO:CO2:H2 1:0.04:1

| Pressure MPa at reactor exit | Temp. °C. at reactor exit | Dew Point °C. | Conversion of CO + CO2 to methanol at gas phase equilibrium, % |
|---|---|---|---|
| 10.0 | 180 | 203.4 | 46.46 |
| 10.0 | 190 | 202.2 | 45.93 |
| 10.0 | 200 | 200.6 | 45.26 |
| 10.0 | 210 | 198.7 | 44.42 |
| 10.0 | 220 | 196.4 | 43.38 |
| 10.0 | 230 | 193.6 | 42.15 |
| 10.0 | 240 | 190.2 | 40.61 |
| 10.0 | 250 | 186.2 | 38.77 |
| 10.0 | 260 | 181.5 | 36.61 |
| 10.0 | 270 | 176.0 | 34.11 |
| 10.0 | 280 | 169.8 | 31.30 |
| 10.0 | 290 | 162.9 | 28.20 |
| 10.0 | 300 | 155.4 | 24.91 |

Figure 2:
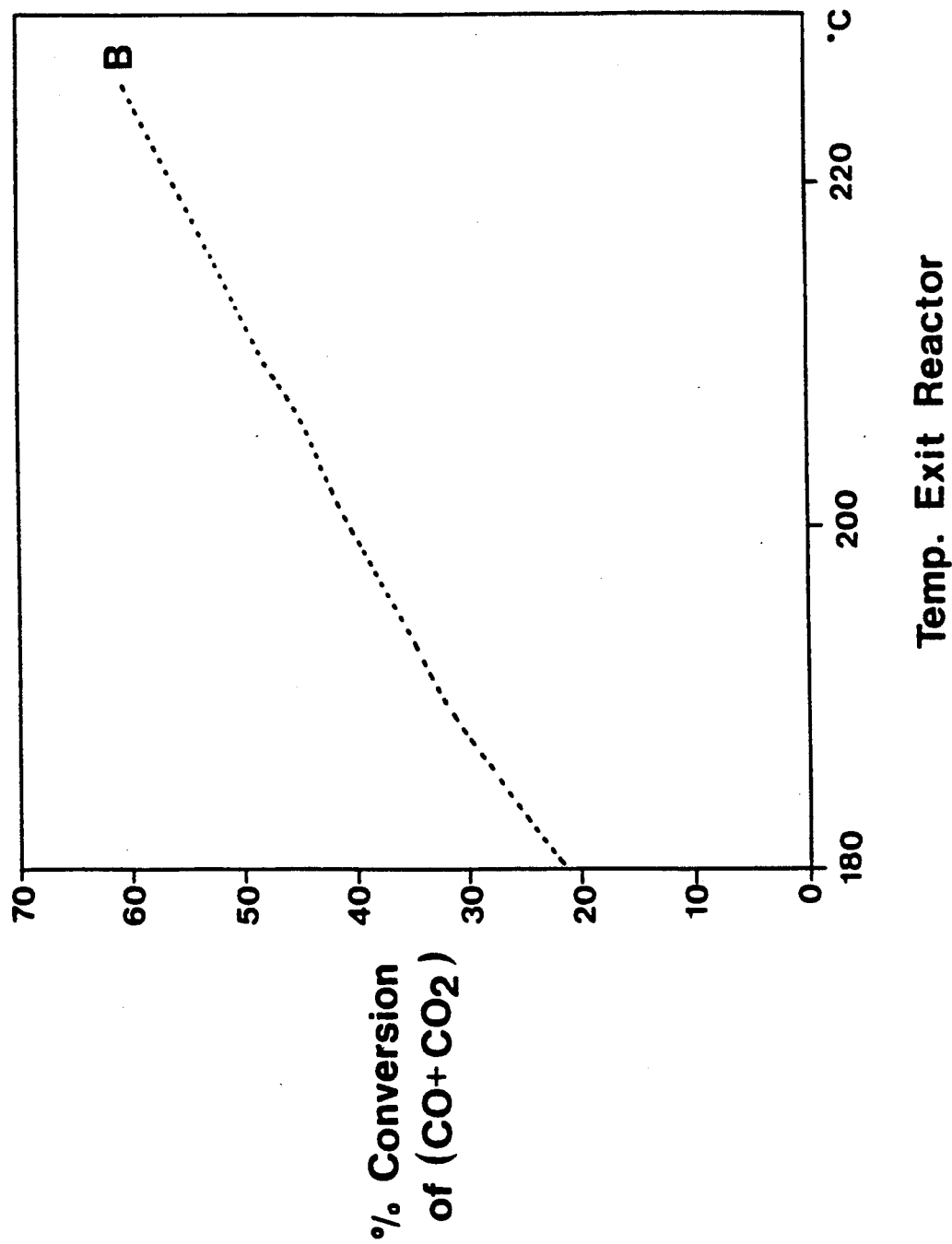
Figure 3:
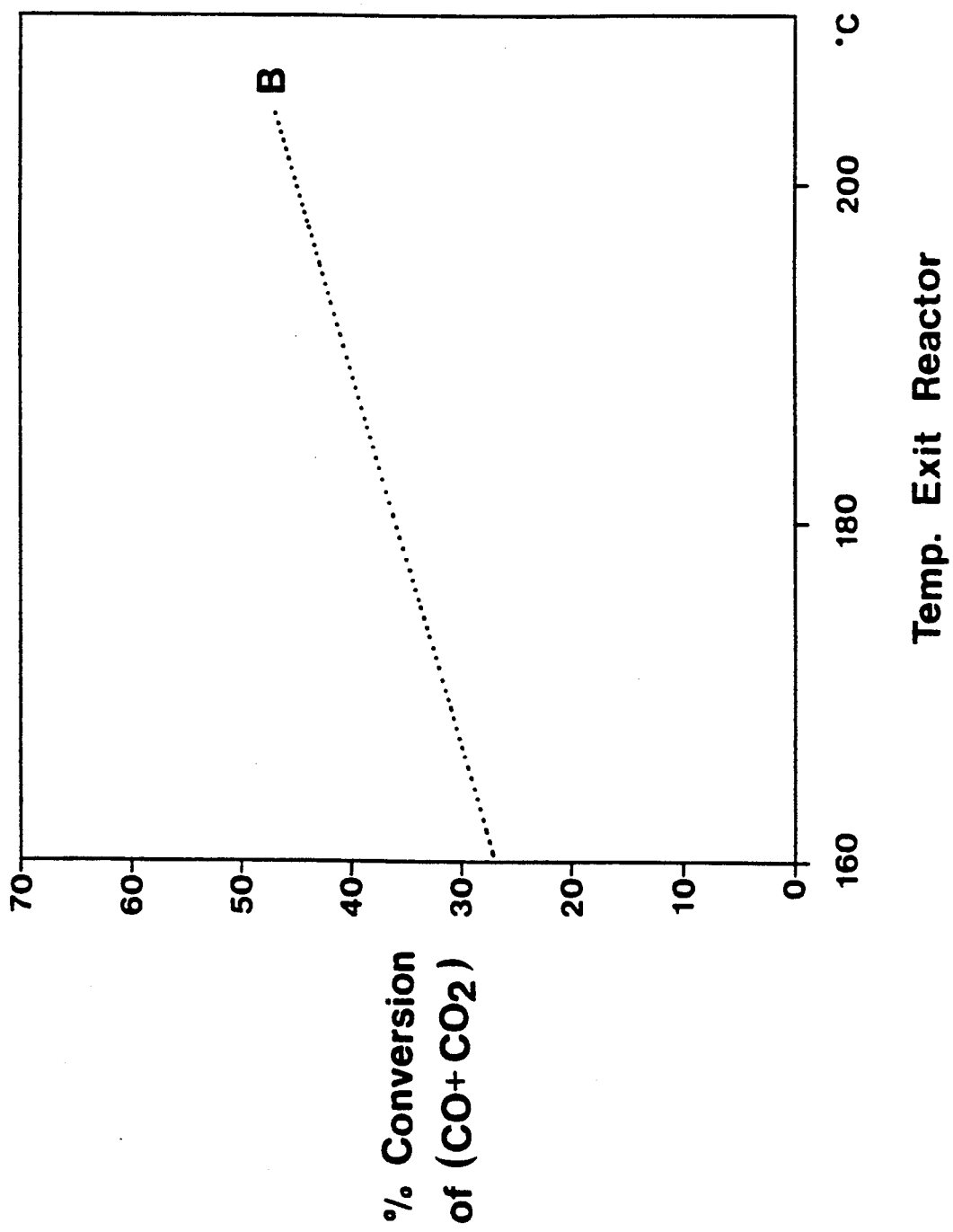

FIG. 1-3 in the drawings are phase diagrams depicting the dew point at reactor exit temperatures and pressures for the synthesis gas compositions specified in Tables 1-3, respectively. The above data for the dew point temperatures and $CO + CO_2$-conversion are calculated at equilibrium conditions for reaction (1) and the shift reaction:

$$CO + H_2O \leftrightarrow CO_2 + H_2 \qquad (2);$$

with the synthesis gas specified in the Tables. In the figures the dew point temperature curves are represented by dotted lines A, B, and C, showing the dew point of the reaction mixture in the catalyst bed at a pressure of 7.5 MPa, 10 MPa and 12.5 MPa, respectively.

As apparent from e.g. Table 1 and the relating FIG. 1 the dew point of methanol is exceeded in synthesis gas comprising CO, $CO_2$ and $H_2$ with a vol. ratio of CO:$CO_2$:$H_2$ of 1:0.1:2.3 at $CO + CO_2$-conversion levels above 87% at 7.5 MPa, above 76% at 10.0 MPa and above 70% at 12.5 MPa pressure and a reactor exit temperature of 210° C.

Figure 4:
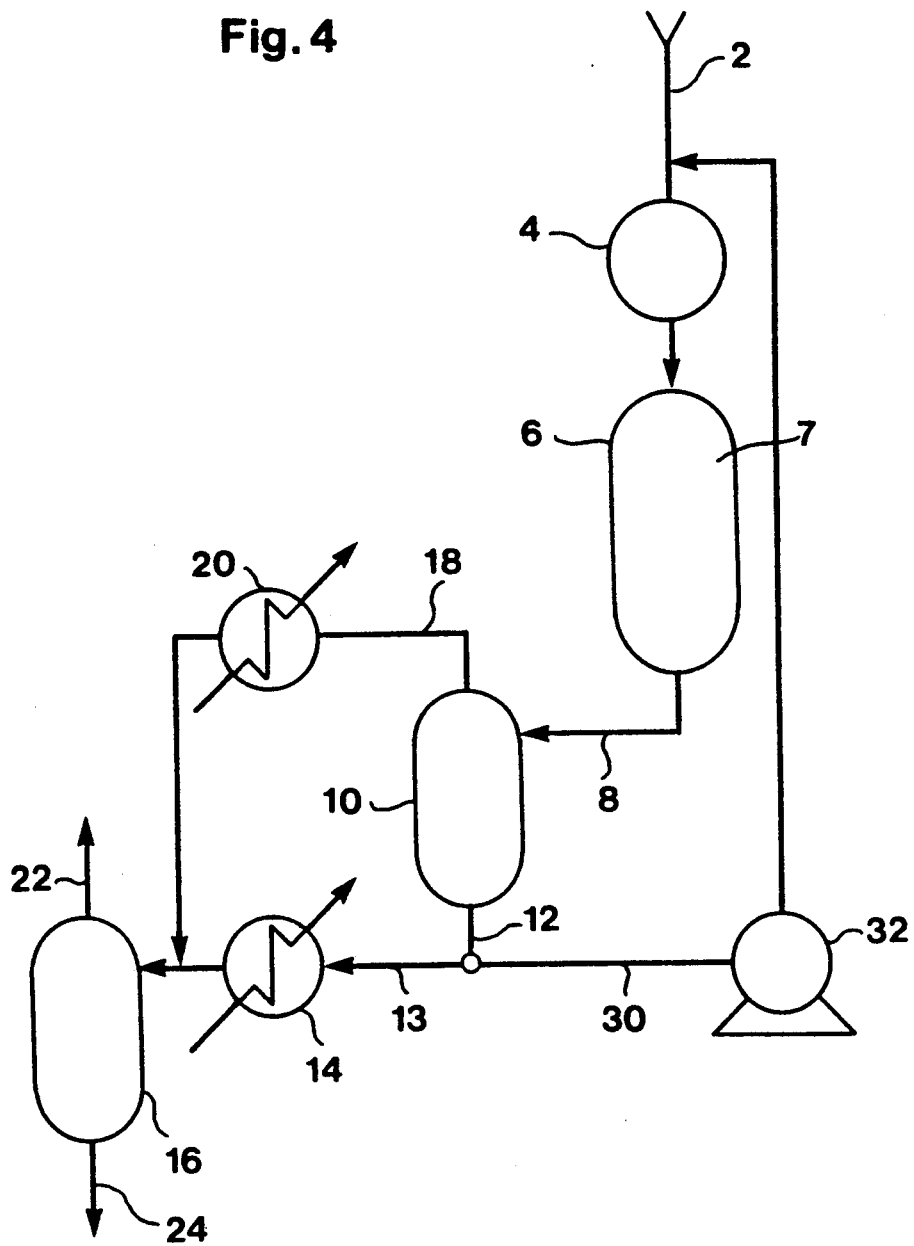
Figure 5:
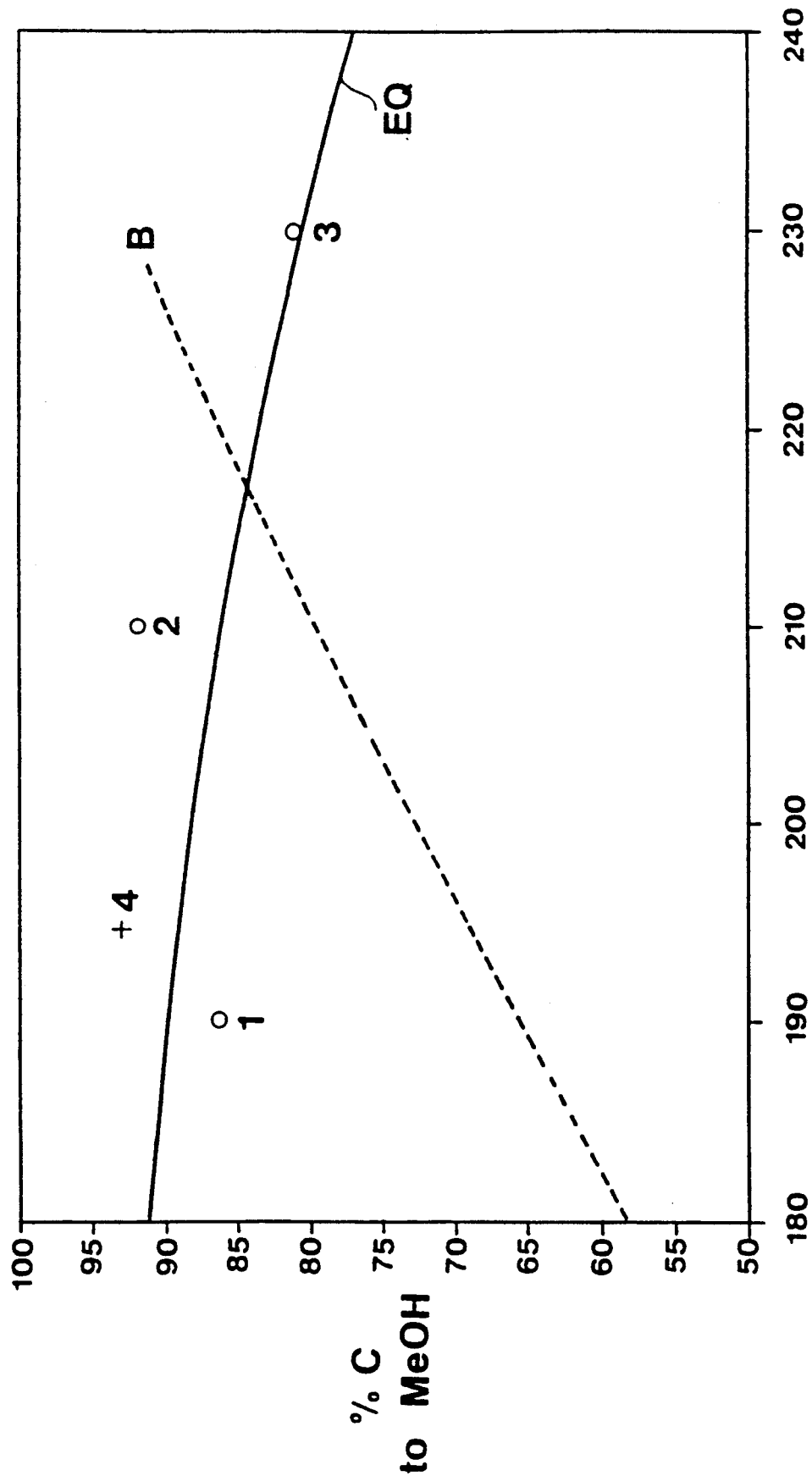

The above features and aspects of the invention are further illustrated in the following Examples by reference to FIG. 4 and 5 in the accompanying drawings, in which FIG. 4 shows a simplified flow sheet of a reactor system for carrying out the methanol synthesis process according to one embodiment of the invention and FIG. 5 depicts the gas phase equilibrium curve of the methanol synthesis reaction together with the dew point and methanol yield obtained by the Examples, which follow.

Referring now to FIG. 4 methanol synthesis gas containing CO, $CO_2$, $H_2$ and small amounts of inert gases are passed in synthesis gas supply line 2 after preheating in preheater 4 to reactor 6. Reactor 6, containing MK-101 methanol synthesis catalyst 7, may be operated under isothermal or adiabatic conditions.

The temperature, pressure and space velocity of the synthesis gas are adjusted to levels where condensation of produced methanol in reactor 6 occurs on the catalyst 7.

Liquid methanol produced in the reactor is withdrawn together with unconverted synthesis gas and gaseous methanol through effluent line 8 and passed to phase separator 10. In separator 10 liquid methanol in the reactor effluent is separated from unreacted gases and gaseous methanol, which through line 18 leave separator 10. Liquid methanol is withdrawn from separator 10 through line 12 and passed through line 13 to cooler 14 arranged in line 13.

Gaseous methanol in line 18 is liquified by cooling in cooler 20 and combined with liquid methanol in line 13. The combined liquid methanol product is recovered in line 24 after further gas-liquid phase separation in separator 16. The remaining gases are vented from separator 16 through vent-line 22.

If necessary small amounts of liquid methanol are recycled from line 12 through line 30 back to synthesis gas supply line 2. The liquid methanol is thereby recompressed by liquid pump 32 and re-evaporated in preheater 4 before being introduced into the reactor 6 together with synthesis gas.

EXAMPLE 1

In this Example 2.4 g of crushed MK-101 methanol catalyst (having a density of 1 kg.) are loaded in reactor 6, which is operated under isothermal conditions.

Synthesis gas with the following composition in vol. %:

| | |
|---|---|
| $H_2$ | 66.51 |
| CO | 29.70 |
| $CO_2$ | 2.08 |
| MeOH | 0.08 |
| Ar | 1.62 | is passed at a flow of 2.57 Nl/h to the reactor (corresponding to a space velocity of 1,071 $h^{-1}$).

At a reactor outlet temperature of 189.9° C. and a pressure of 9.5 MPa 86.57% of $CO + CO_2$ in the synthesis gas are converted to methanol. The vapour fraction of the reactor effluent is 58.4%, indicating that the dew point in the catalyst bed has been exceeded. The results from this Example are further illustrated in FIG. 5 showing the methanol yield obtained by the above process indicated by marker 01.

EXAMPLE 2

By using the same process set-up as described in Example 1 synthesis gas with the following composition in vol. %

| | |
|---|---|
| $H_2$ | 66.37 |
| CO | 29.72 |
| $CO_2$ | 2.15 |
| MeOH | 0.08 |
| Ar | 1.64 | is passed at a flow of 2.57 Nl/h to the reactor.

At a reactor outlet temperature of 210.0° C. and a pressure of 9.5 MPa 92.16% of $CO + CO_2$ in the synthesis gas are converted to methanol. The vapour fraction of the reactor effluent is 58.2%, indicating that the dew point in the catalyst bed has been exceeded, as illustrated by FIG. 5 with marker 02.

As further apparent from FIG. 5 the gas phase equilibrium curve (EQ) for the methanol reaction (1) and shift reaction (2) has been overcome, resulting in a conversion level of $CO + CO_2$ higher than predicted by gas phase thermodynamics.

EXAMPLE 3

By using the same process set-up as described in Example 1 synthesis gas with the following composition in vol. %:

| | |
|---|---|
| $H_2$ | 66.42 |
| CO | 29.68 |
| $CO_2$ | 2.13 |
| MeOH | 0.10 |
| Ar | 1.65 | is passed at a flow of 2.57 Nl/h to the reactor.

At a reactor outlet temperature of 229.9° C. and a pressure of 9.5 MPa 82.57% $CO + CO_2$ in the synthesis gas are converted to methanol.

The vapour fraction of the reactor effluent is 100%, indicating that no methanol condensation on the catalyst has occurred. Thus the dew point curve has not been exceeded, as further shown in FIG. 5 by marker 03.

EXAMPLE 4

In this Example reactor 6 is a Dowtherm cooled pilot reactor loaded with 3.32 kg of MK-101 methanol synthesis catalyst in the form of pellets as supplied by Haldor Topsoe A/S, Denmark.

Synthesis gas with the following composition in vol. %:

| | |
|---|---|
| $H_2$ | 58.21 |
| CO | 25.20 |
| $CO_2$ | 1.70 |
| MeOH | 13.94 | is passed to the reactor at a flow of 3.87 $Nm^3$:/h (corresponding to a space velocity of 1,166 $h^{-1}$). The Dowtherm temperature is kept at 194° C. and the pressure in the reactor is 9.2 MPa.

The composition of the reactor effluent is analyzed to 12.8 vol. % $H_2$; 4.62 vol. % CO; 3.04 vol. % $CO_2$ and 80.64 vol. % $CH_3OH$, corresponding to a conversion of 92.6% $CO + CO_2$ to methanol.

As seen from FIG. 5 at a conversion level of 92.6% marked as +4 in the figure the dew point of the reaction mixture has been exceeded leading to condensation of methanol on the catalyst. Furthermore, the gas phase equilibrium curve (EQ) has been overcome, resulting in conversion levels higher than predicted by gas phase thermodynamics.

We claim:

1. A method of preparing methanol, comprising the steps of reacting a synthesis gas comprising hydrogen, carbon monoxide and carbon dioxide in a fixed bed of methanol synthesis catalyst at a pressure and a temperature where condensation of liquid methanol occurs on the catalyst, and maintaining the temperature of the catalyst bed at a temperature below the dew point temperature of the methanol wherein liquid methanol is produced, and wherein the reaction conditions comprise a catalyst bed outlet temperature of between 170° and 240° C. and a pressure of between 5 and 20 MPa.

2. The method of claim 1, wherein a part of the condensed methanol as prepared in the catalyst bed is recycled from the catalyst bed effluent to the inlet of the catalyst bed.

3. The method of claim 1, wherein the synthesis gas comprises up to 70 vol. % CO, up to 25 vol. % $CO_2$ and 25-75 vol. % $H_2$.

4. The method of claim 1, wherein the reaction conditions include a catalyst bed outlet temperature of between 180° and 220° C. and a pressure of between 7 and 13 MPa.

5. The method of claim 4, wherein the reaction conditions include a catalyst bed outlet temperature of between 190° and 210° C. and a pressure of about 10 MPa.

6. The method of claim 1, further including a conversion level of $CO+CO_2$ in the synthesis gas of at least 20%.

7. The method of claim 6, further including a conversion level of $CO+CO_2$ in the synthesis gas of at least 40%.

8. The method of claim 7, further including a conversion level of $CO+CO_2$ in the synthesis gas of at least 60%.

9. The method of claim 3, wherein the synthesis gas comprises 10-60 vol. % CO, 2-15 vol. % $CO_2$ and 30-60 vol. $H_2$.

10. The method of claim 9, wherein the synthesis gas comprises 31 vol. % CO, 2 vol. % $CO_2$ and 67 vol. % $H_2$.

11. The method of claim 1, further comprising the step of passing the synthesis gas at a space velocity of 1,071 $h^{-1}$ to the catalyst bed.

12. The method of claim 1, further comprising the step of passing the synthesis gas at a space velocity of 1,166 $h^{-1}$ to the catalyst bed.

* * * * *